United States Patent [19]
Shonfeld

[11] Patent Number: 5,370,620
[45] Date of Patent: Dec. 6, 1994

[54] SINGLE USE HYPODERMIC SYRINGE

[76] Inventor: David Shonfeld, 20 Breuer Ave., Great Neck, N.Y. 11023

[21] Appl. No.: 151,812

[22] Filed: Nov. 15, 1993

Related U.S. Application Data

[63] Continuation-in-part of Ser. No. 997,313, Dec. 28, 1992, abandoned.

[51] Int. Cl.$^5$ .............................................. A61M 5/00
[52] U.S. Cl. ...................................... 604/110; 604/218
[58] Field of Search ............... 604/110, 218, 219, 187, 604/232, 234, 220, 228

[56] References Cited

U.S. PATENT DOCUMENTS

| | | | |
|---|---|---|---|
| 1,008,017 | 11/1911 | Crittenden | 604/218 |
| 3,823,715 | 7/1974 | Holanek et al. | 604/218 X |
| 4,391,272 | 7/1983 | Staempfli | |
| 4,979,943 | 12/1990 | Trenner | |
| 4,986,820 | 1/1991 | Fischer | 604/218 |
| 5,047,017 | 9/1991 | Koska | 604/110 |

Primary Examiner—John D. Yasko
Attorney, Agent, or Firm—Levisohn, Lerner & Berger

[57] ABSTRACT

A non-reusable syringe is provided with an annular locking groove having a seat proximal to the rear end of the barrel and a second annular locking groove with a second seat located near the proximal end of the barrel. The plunger for the non-reusable syringe is provided with a flexible disc preferably located directly behind the piston head so that when the plunger is inserted with the barrel, the disc can bend upwardly when sliding the plunger downwardly past the first seat of the annular locking groove and, yet, proximal relative movement of the plunger with respect to the barrel is precluded by the cooperation of the disc and the locking groove. When the plunger is fully pushd in the distal direction, the disc, again, can pass in one direction beyond the second locking groove and its seat and, yet, reciprocation or proximal movement of the plunger with respect to the barrel is precluded by the mechanical interaction of the disc with respect to the second locking groove and seat. In this manner, a non-reusable syringe is provided.

24 Claims, 14 Drawing Sheets

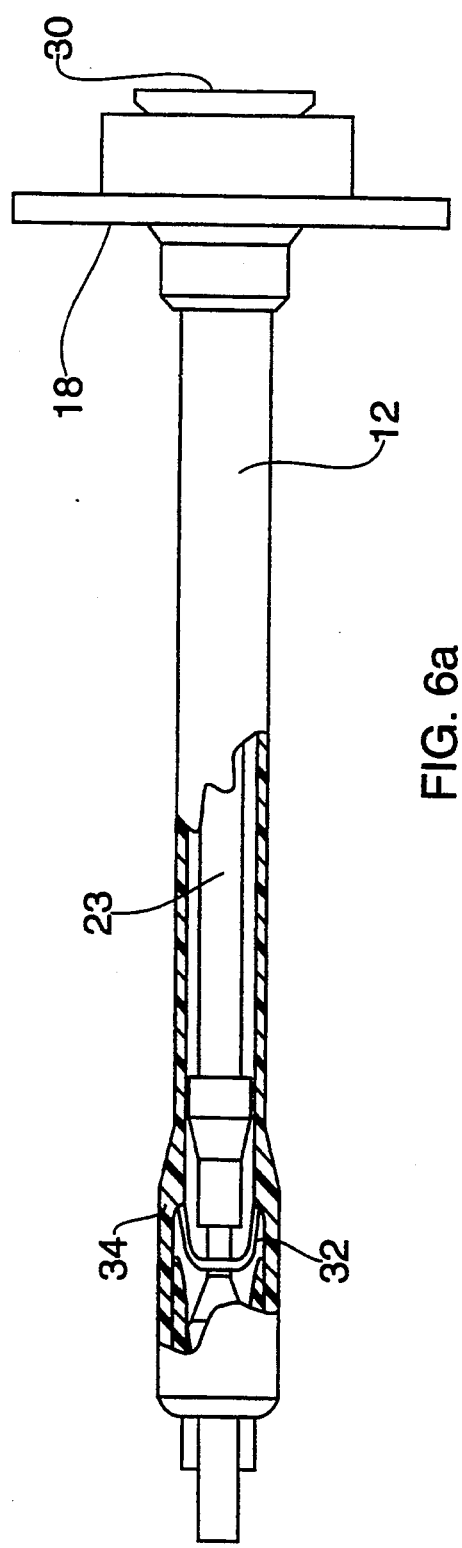

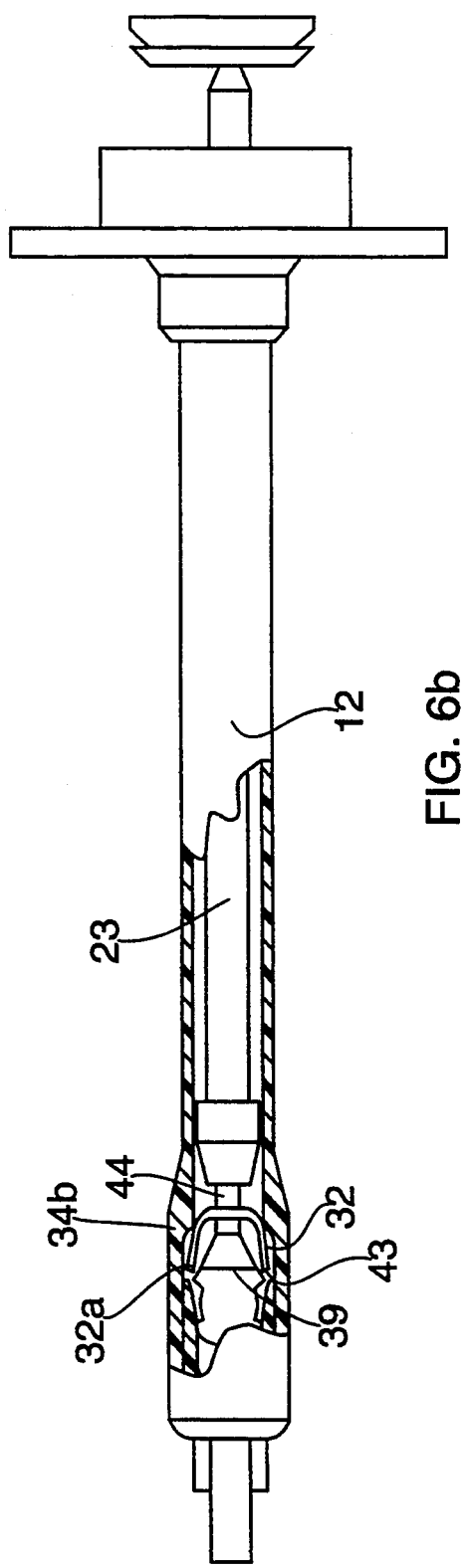

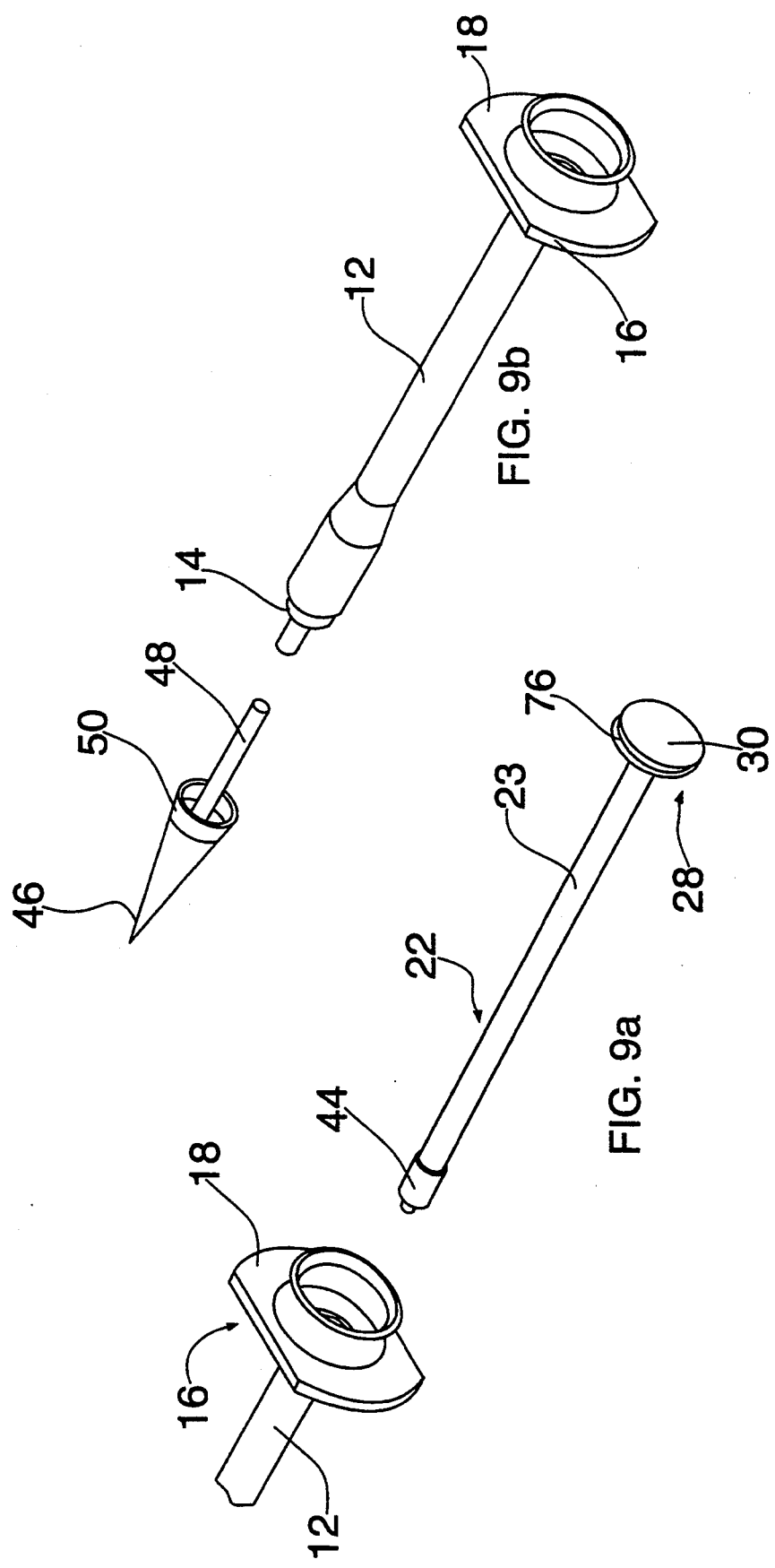

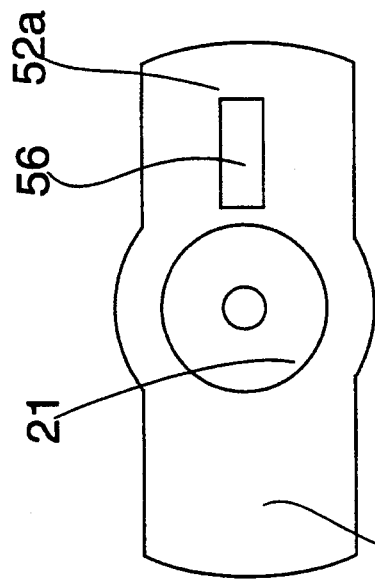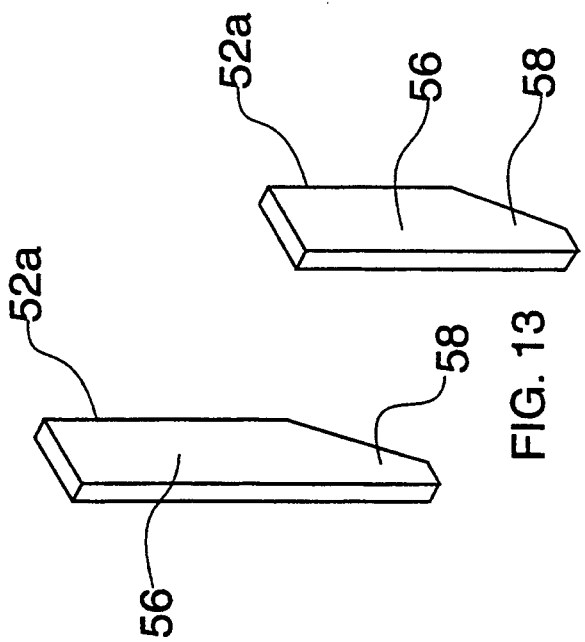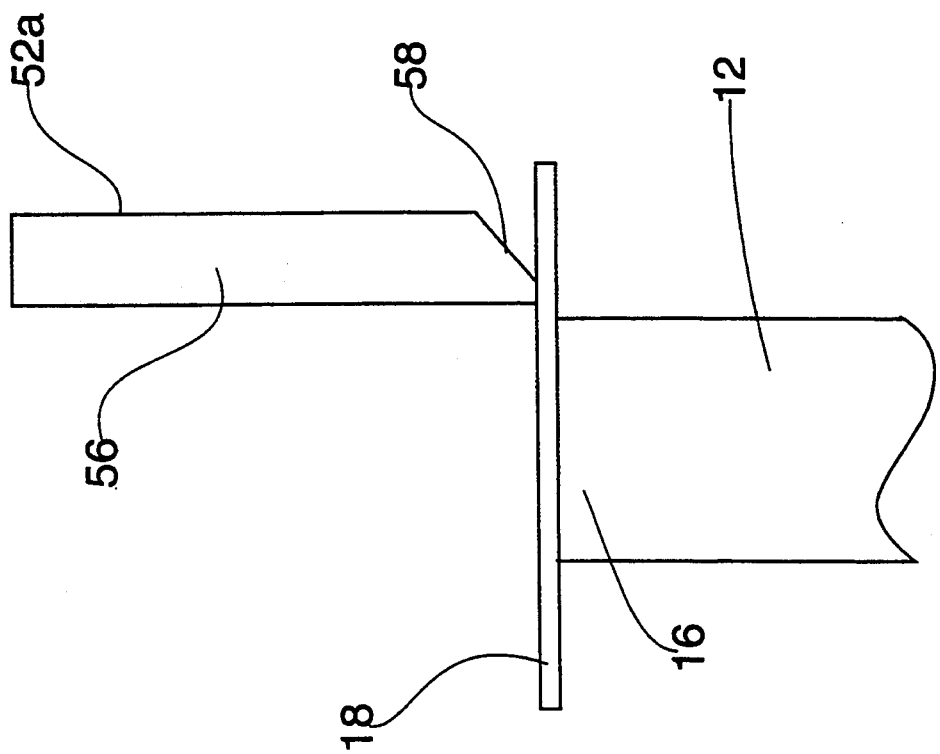

SINGLE USE HYPODERMIC SYRINGE

RELATED APPLICATIONS

This application is a continuation-in-part of pending U.S. patent application Ser. No. 07/997,313, filed Dec. 28, 1992 now abandoned.

BACKGROUND OF THE INVENTION

The instant invention relates generally to medical tools and more specifically it relates to a non-reusable, single use hypodermic syringe. Because diseases such as AIDS are easily transmitted between individuals by the reuse of hypodermic needles, there is a vital requirement for a hypodermic syringe which permits only one time use. It is this requirement that the instant invention is designed to satisfy.

Numerous medical tools have been provided in the prior art that are adapted to help in the assistance in treating various illnesses and injuries to people. While these units may be suitable for the particular purpose which they address, they would be as suitable for the purposes of the present invention as heretofore described.

There are several hypodermic syringe constructions with non-retractable drive pistons. One such prior structure is that identified in U.S. Pat. No. 4,391,272 entitled "Disposable Syringe", issued to Jackie Staempfli which discloses a segmented disk 6 attached to a plunger 4 lockable in annular grooves 5 so that the plunger 4 is capable of being moved forwardly with minimum resistance between disk 6 and the inner wall of the cylinder, but when the plunger is moved fully forward, disk 6 is locked in groove 5 preventing upwardly rearwardly movement of the plunger.

U.S. Pat. No. 4,493,703 issued to Ida M. Butterfield entitled "Hypodermic Syringe Cartridge With Non-Retractable Piston" illustrates another resilient disk-like element 32 which is flexed rearwardly permitting the plunger to move forwardly in the barrel. Disk-like element 32 is captured in annular grooves formed by a ratchet surface formed on the inner wall of the barrel. In this manner, the flexed disk-like member 34 prevents rearward movement of the plunger, including the additional resistance to movement required to force the disk-like member from its pre-stressed rearwardly flexed position.

U.S. Pat. No. 4,979,943 issued to Lewis E. Trenner entitled "Single Use Hypodermic Needle" illustrates yet another form of lock to prevent retraction of the plunger after dispensing of the fluid through the syringe by providing a reversal stop 86 which bears against end wall 16.

Each of these prior art devices requires that the groove which locks the disk from rearward movement be substantially perpendicular to the axis of the plunger. Since swinges can be of varying sizes, a square shaped groove may not easily be achievable for one cc. syringes. The thickness of the barrel and the tolerances achievable do not allow for sufficient accuracy to produce reliable syringes of such small sizes. Further, the manner of preventing reverse movement of the plunger merely relies upon the mating bearing surfaces between the rear wall of the disk and front wall of the seat formed by the groove. be possible to actually use sufficient force to bend the disk and pull it out of the groove allowing the plunger to be removed from the barrel.

SUMMARY OF THE INVENTION

An object of the present invention is to provide a single use hypodermic syringe that will overcome the shortcomings of the prior art devices.

Another object is to provide such a syringe in which the plunger cannot be removed intact from the barrel after it has been pushed toward the needle to dispense the fluid carried therein.

An additional object is to provide such a syringe that contains a structure to prevent the plunger from accidentally being pushed into the barrel before use.

Yet another object is to provide a single shot syringe which may be susceptible to easy manufacture in one cc and other sizes.

Another object of this invention is to provide a structure which prevents removal of the plunger from the barrel by physically blocking such movement and making it impossible for the plunger to be moved out of the barrel after it is used without completely destroying the syringe.

A further object is to provide a one-shot syringe that is simple and easy to use.

A still further object is to provide such a syringe that is economical in cost to manufacture.

Further objects of the invention will appear as the description proceeds.

To accomplish the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWINGS

The figures in the drawings are briefly described as follows:

FIG. 6a is a view similar to FIG. 6 showing the plunger and disk moved toward the needle end;

FIG. 6b is another view similar to FIG. 6 illustrating the plunger and disk in position to prevent the plunger from being withdrawn from the barrel after use of the syringe;

FIG. 7 is a cross sectional view of the plunger in the barrel with the plunger inserted in the barrel as shown in FIG. 6a;

FIGS. 9a and 9b are diagrammatic perspective views with parts broken away illustrating a first embodiment of a limiting device incorporated therewith;

FIG. 11 is an enlarged diagrammatic elevational view with parts broken away illustrating a third type of limiting device;

FIG. 12 is a top view taken in the direction of arrow 12 in FIG. 11;

FIG. 13 is a diagrammatic perspective view illustrating various sized third type limiting devices.

DETAILED DESCRIPTION

Figure 1:
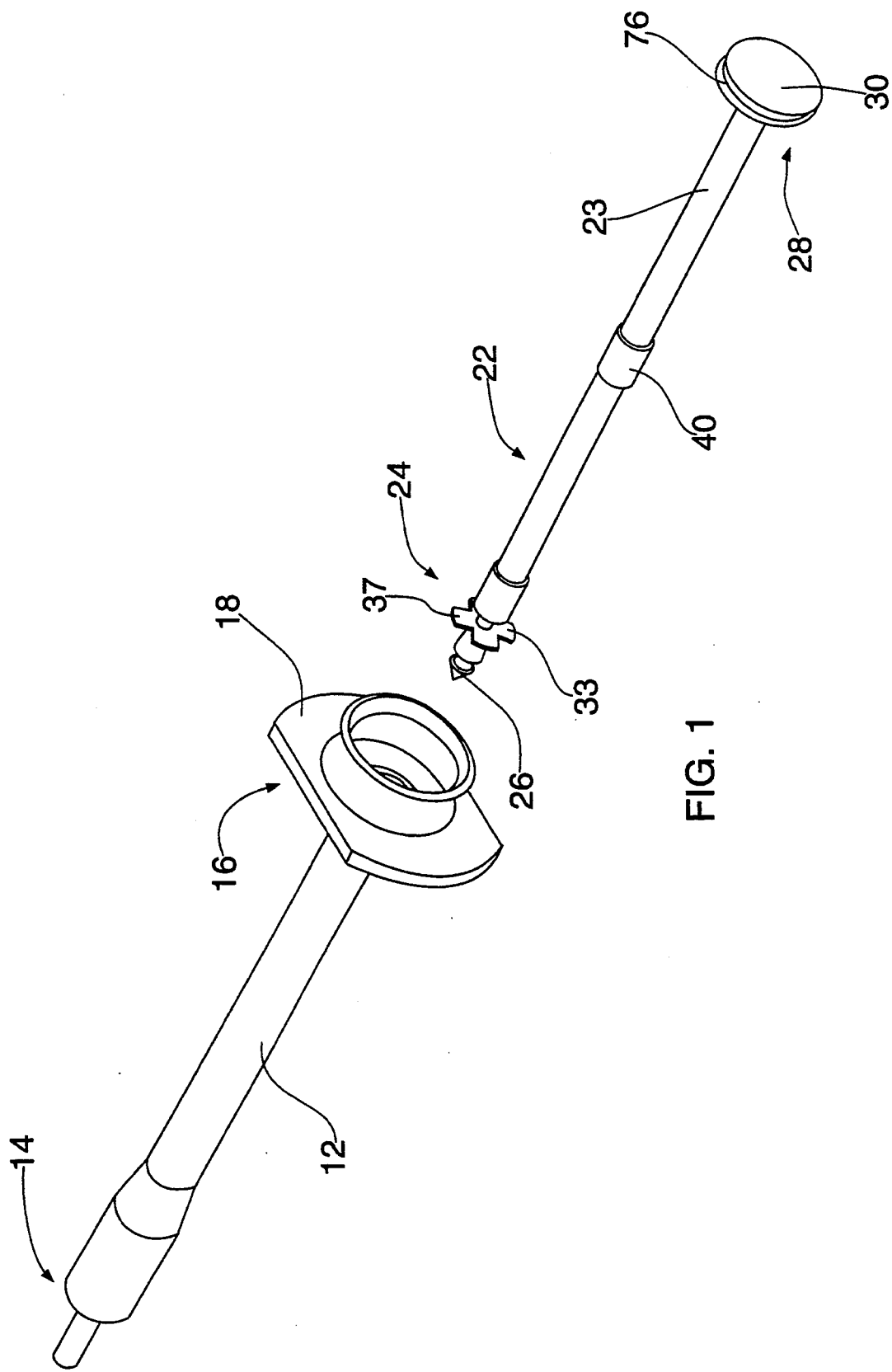
FIG. 1 is a diagrammatic perspective view of the instant invention showing the plunger and barrel as separate components.
Figure 2:
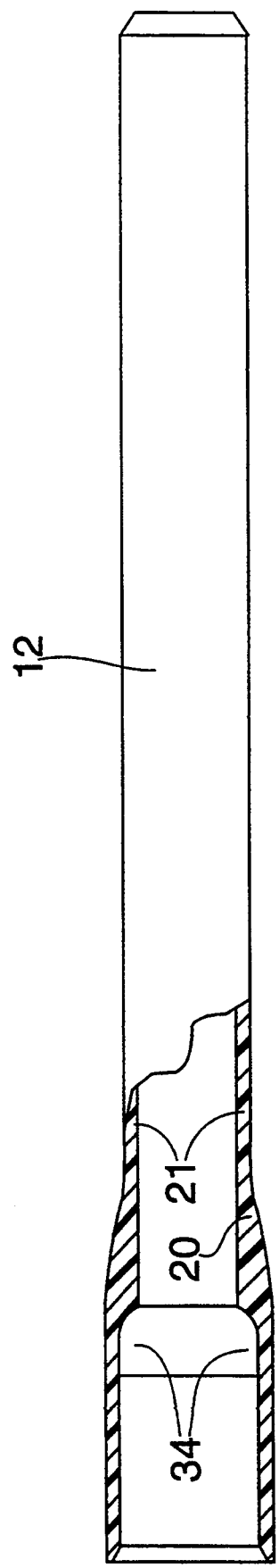
FIG. 2 is an enlarged elevational view partly in section of the barrel thereof.

Turning now descriptively to the drawings, in which similar reference characters denote similar elements throughout the several views, the Figures illustrate a single use or one-time use syringe 10 which consists of a barrel 12 having a forward end 14 for attachment of a hypodermic needle, a rearward end 16 with a finger flange 18 and a cylindrical chamber 20 formed of a first bore partially therethrough. The syringe 10 includes a plunger 22 which comprises a rod 23 having a forward end 24 with a piston head 26 and a rearward end 28 with a thumb rest 30 axially aligned with rod 23. A disk 32 is attached to the forward end and retains the piston head 26 of the plunger 22 within the barrel 20 after the plunger 22 is pushed toward the forward end to dispense the fluid carried therein through the needle. The disk 32 is shown made of a cross-like structure 33, but the disk could be annular or irregularly shaped.

Figure 4:
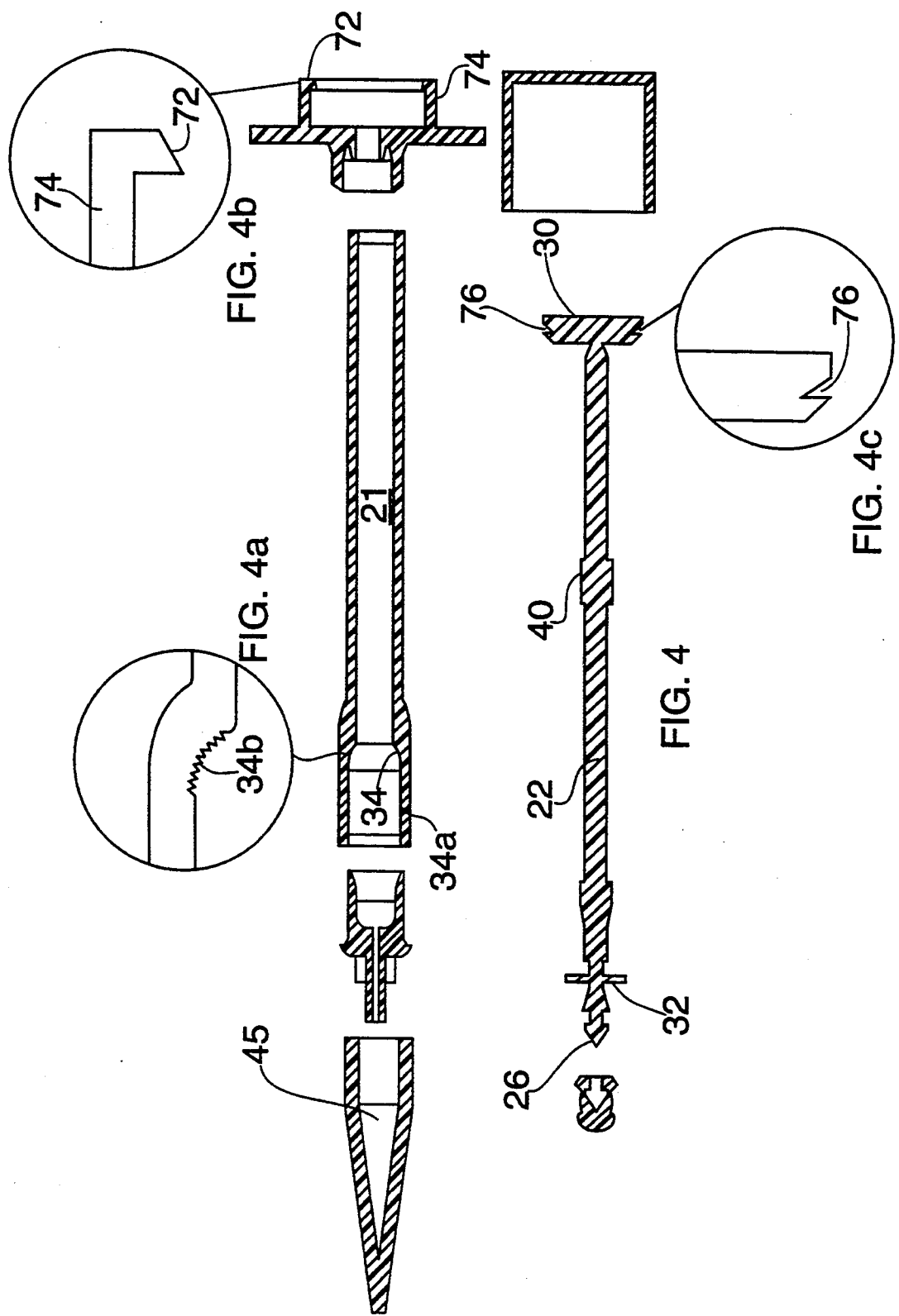
FIG. 4 is an enlarged cross sectional view of the plunger and barrel with parts broken away as indicated in FIGS. 4a, 4b and 4c.
Figure 5:
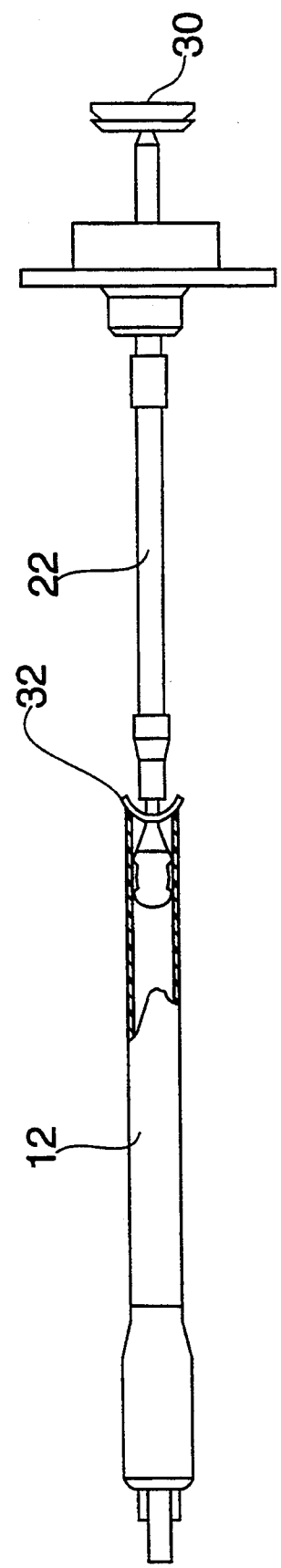
FIG. 5 is an enlarged diagrammatic elevational view partially in section with parts broken away, illustrating the plunger initially inserted into the barrel of the syringe.
Figure 6:
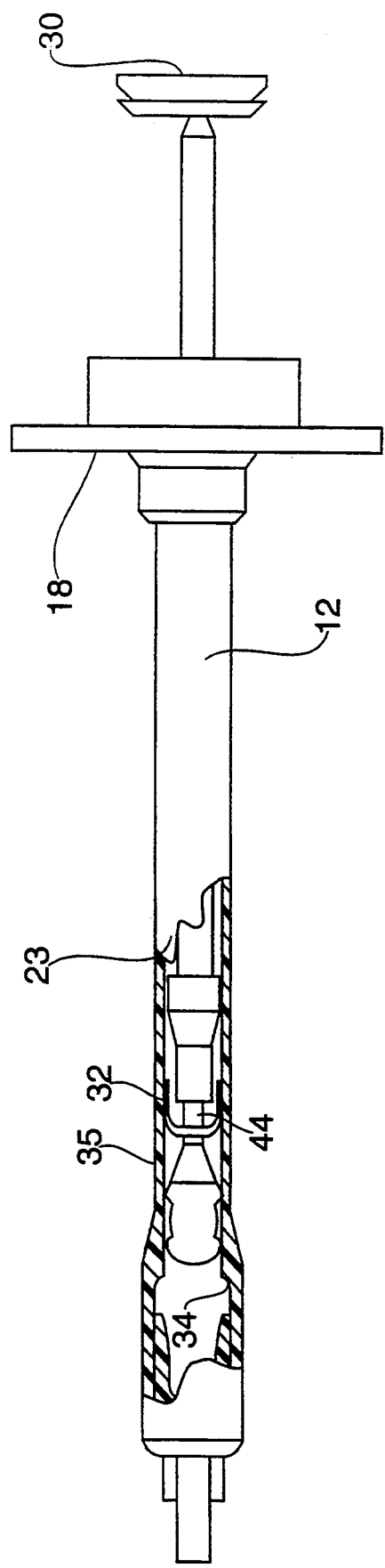
FIG. 6 is a diagrammatic elevational view with parts broken away and partially in section illustrating the flexed disk attached to the plunger prior to ejection of the fluid from the syringe.

The disk 32 may be integrally formed with or attached to the forward portion 24 of the plunger 22. The disk is flexed normally concave rearward as the disk 32 is inserted into bar-rel 20 (see FIG. 5) because the disk 32 is wider in circumference than is the diameter 25 of the first bore 21 of cylindrical chamber 20. The first bore 21 expands outwardly into a widened annular second bore 34a forwardly of the first bore 21 along a curved wall segment 34. (see FIGS. 4 and 6—6b) The diameter of second bore 34a is slightly smaller than the diameter of disk 32.

The curved wall segment 34 formed in chamber 20 may be formed by using a collapsible core which generates an undercut of the desired configuration. As a preferred embodiment, and as shown in FIG. 4a, the surface 34b of the wall 34 is rough to enhance the frictional engagement of the disk 32.

Although an expanding wall section 34 is described, the invention including the generation of any outwardly rounded surface, even where the surface again reverses its direction so as to form a third smaller bore forwardly of the second, what is required is that a surface is formed which does not permit the disk to move rearwardly after the syringe is used with out having to reverse its flex.

Figure 3:
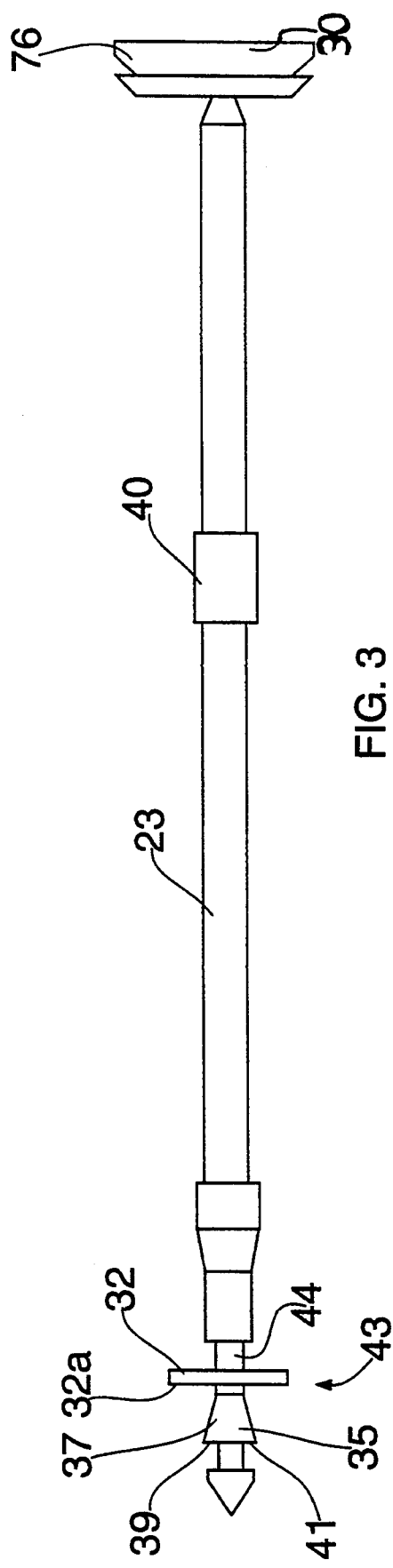
FIG. 3 is an enlarged elevational view of the plunger thereof.

The forward portion 24 of plunger 22 (FIG. 3) also has a widened frustoconical bearing section 35 integrally formed with the barrel with a narrow portion 37 of the frustoconical section adjoining the center portion of disk 32. The widest portion 39 of frustoconical section 35 has a diameter 41 which is slightly smaller than the diameter 25 of the first bore 21. As a preferred embodiment, the annular distance between the widest portion 39 and the inner wall 21 is less than the thickness 43 of disk 32.

In operation, so long as the plunger 22 has not yet ejected its fluid, the plunger may be moved rearwardly to draw fluid into the forward chamber 45 of the barrel 20. There is minimal interference with forward or rearward movement of the plunger 22 as long as the plunger is in a position where disk 32 has not yet entered the curved wall area 34.

When the plunger 22 is fully inserted into the barrel 20, the disk 32 moves into the second bore 34a and remains in the initial concave rearward configuration. In this position the plunger tends to resist removal from the barrel because of the resistance of the disk to reversing its flexed configuration.

This invention provides an additional safety which further prevents the user from removing the plunger from the barrel after the fluid has been ejected because as the plunger moves rearwardly toward the first bore 21 from its most forward position disk 32 moves rearwardly in curved section 34. As the edge of the disk contacts the wall of section 34, the disk 32 begins to reverse its initial flexed position because of the friction between the edge of disk 32 and wall 34. As described above, this alone may provide enough resistance to prevent withdrawal of the plunger because of the compressive forces on the disk resisting reversal of its flexed position. The disk 32 can be formed of suitable resilient plastic material or any other material which would tend to resist the reversal of the flexed disk configuration and be safe for use in a medical device.

In order to fully ensure against further rearward movement or withdrawal of the plunger 22 from the barrel 12, the outer peripheral portion 32a of the disk 32 becomes jammed between the first groove 21 in the area 34 because the widest portion 39 of frustoconical bearing section 35 jams against the disk 32 as the disk moves ream rearwardly in the region 34. It is impossible to pull plunger 22 further rearwardly without destroying. The syringe and separating the plunger from the forward portion 26 thereof.

Figure 7:
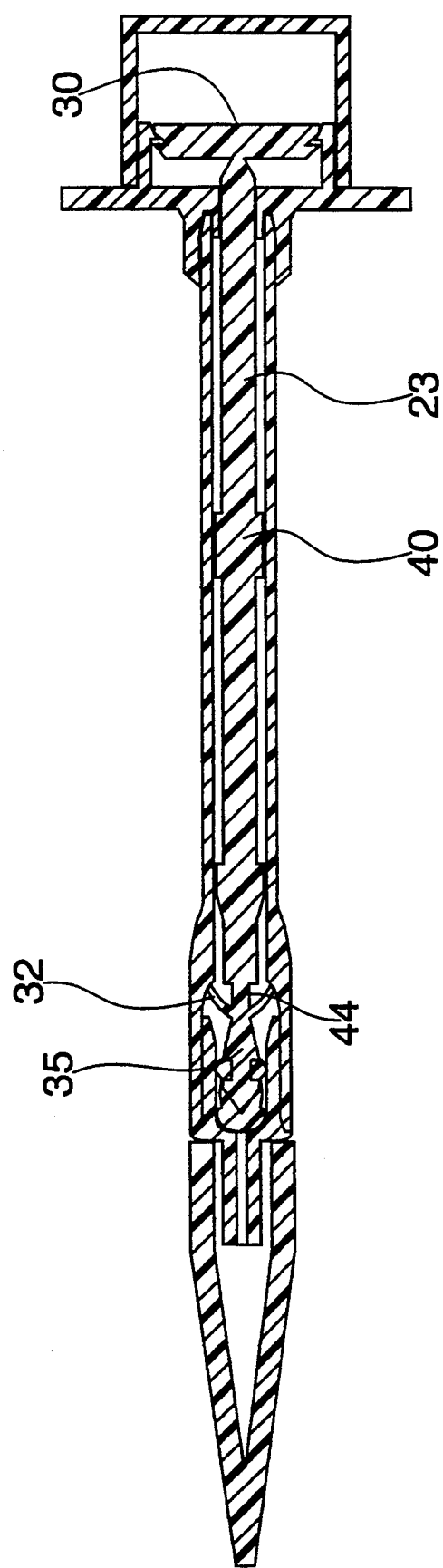
Figure 7A:
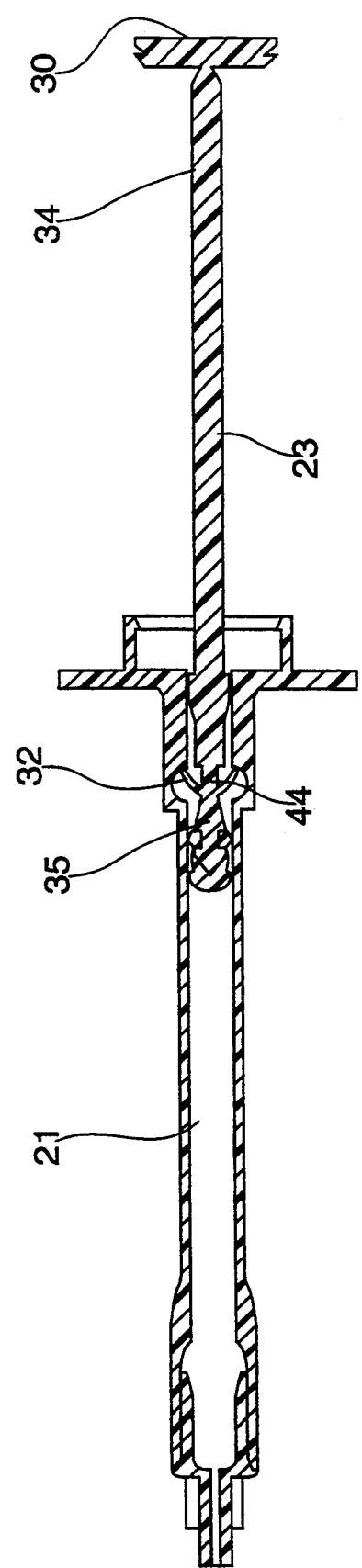
FIG. 7a is an alternative embodiment of a blocking means preventing retraction of the plunger from the syringe prior to use of the syringe.

As a further feature of this invention, the plunger is locked into a fixed position with respect to said barrel by means of a finger portion 72 (FIG. 4b) formed inwardly from a rearwardly projection 74 projecting rearwardly from finger flange 18 which locks into groove 76 (FIG. 4c) formed on the periphery of the thumb rest 30. The distance that the projection 74 extends rearwardly from the finger flange 18 is chosen so that when the plunger is fully inserted, the finger portion 72 locks into groove 76 (See FIG. 7).

The plunger 22 further includes a collar portion 40 fixedly or slidably located on rod 23 adjacent the disk 32. Rearward end 10 of the barrel 12 comprises the flange 18 (FIG. 4) having a reduced inner annular axial blocking wall 42 which sits at the end of chamber 20. Collar portion 40 abuts against blocking wall 42 and as plunger 22 is further pulled outwardly a forward collar 44 bears against collar 40 locking the plunger 22 in the barrel 12.

As a further safety feature to prevent the plunger being removed from the barrel before use, a second widened tapered surface 70 is formed in the inner wall 21 of the barrel located between the first tapered surface 34 and the rear 16. Preferably such second tapered surface 70 is nearer the rear.

Figure 8:
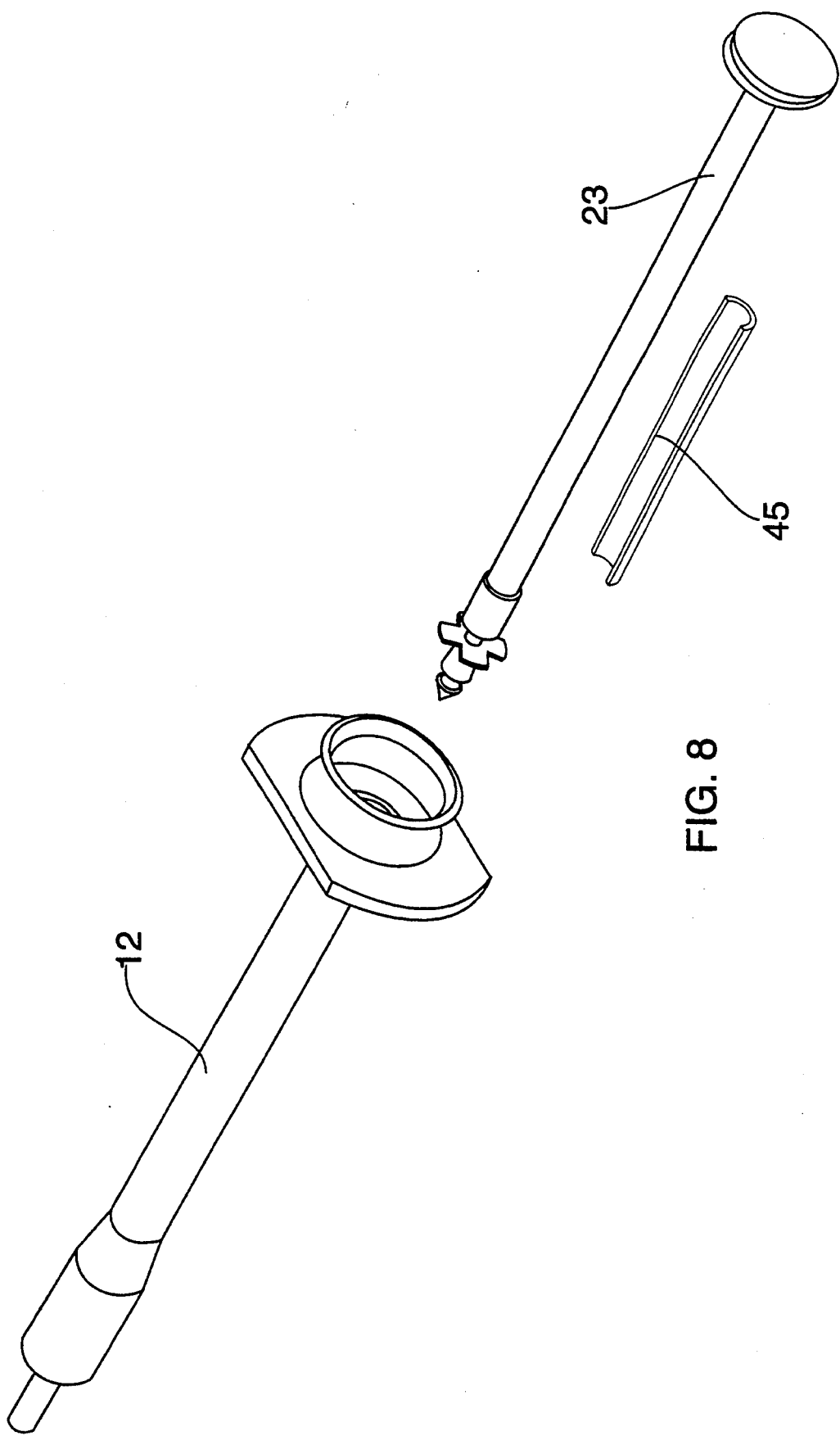
FIG. 8 is a diagrammatic perspective view of another embodiment of this invention preventing retraction of the plunger from the syringe prior to use of the syringe.

FIG. 8 illustrates another embodiment of a rear collar in which a slidable partial cylinder 45 slides on rod 23 to block rearward movement of the plunger from the barrel before the syringe is used.

Referring to FIGS. 9a and 9b, a protective cap 46 has an elongated rod 48 extending from a wide end 50 of the cap 46. The protective cap 46 can be fitted onto the forward end 14 of the barrel 12 before attachment of the hypodermic needle and can either be a friction fit or threadedly engaged therewith. The elongated rod 48 extends into the chamber 20 past the section 34 to prevent the piston head 26 from accidentally sliding forward before appropriate use of the single shot syringe 10 for one time injecting of medication into a patient.

Figure 10B:
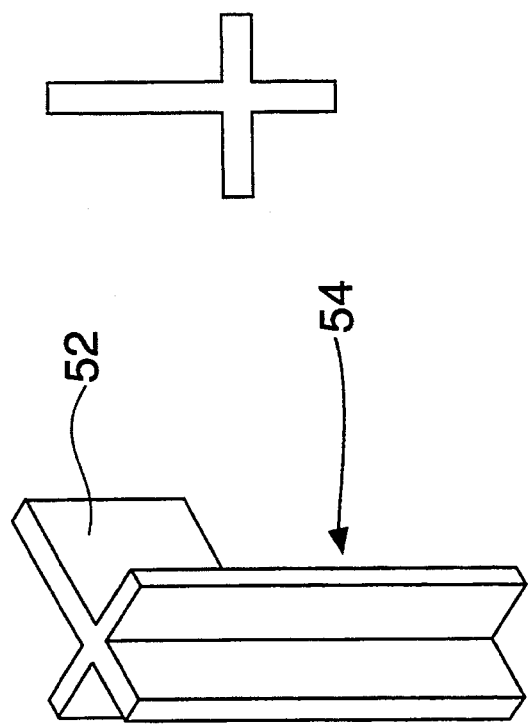
FIGS. 10a and 10b are enlarged diagrammatic perspective views of a second type limiting device per se.
Figure 10A:
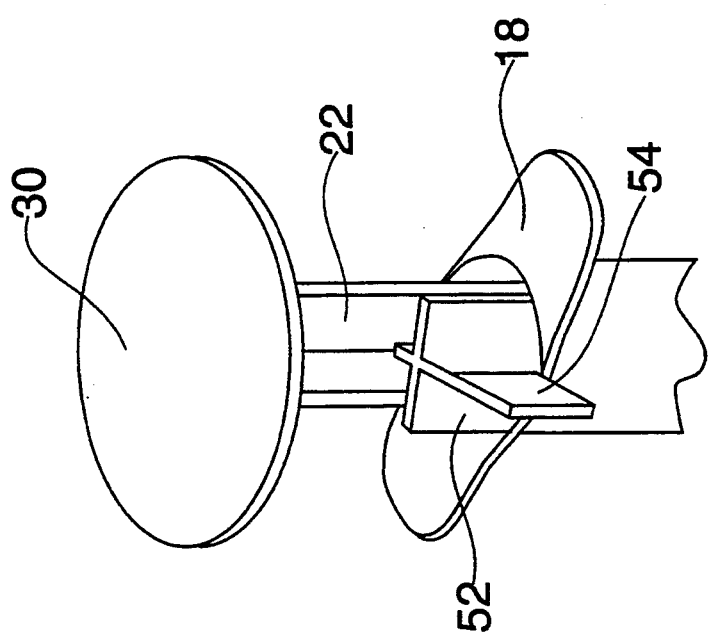

A second alternate arrangement 52 is for restricting the plunger 22 from being accidentally pushed fully forwardly in the chamber 20 of the barrel 12. The restricting arrangement 52 is shown in FIGS. 10a and 10b and comprises a limiting device 54 insertable into the chamber 20 at the rearward end 16 of the barrel 12. If the plunger 22 is accidentally depressed, the thumb rest 30 will contact the limiting device 54 and stop. A third alternate restricting arrangement 52a, as shown in FIGS. 11, 12 and 13 is a limiting device 56 connected to and extending upwardly from one side of the finger flange 18. If the plunger 22 is accidentally depressed, the thumb rest 30 will contact the limiting device 56 and stop. The limiting device 56 incudes a narrow tapered portion 58 integrally connected to the finger flange 18, so that the limiting device 56 can be broken off and removed therefrom to allow the plunger 22 to be depressed into the barrel 12 for appropriate one time use.

While certain novel features of this invention has been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A non-reusable syringe comprising:
   a) a barrel having a forward end for attachment to a hypodermic needle, a rearward end with a finger flange and a cylindrical chamber having an inner wall with a first bore partially therethrough;
   b) a plunger having a forward end with a piston head and a rearward end wth a thumb rest;
   c) said cylindrical chamber widening forwardly in a curved wall segment into a second wider bore portion formed in the inner wall of said cylindrical chamber;
   d) said plunger having a flexible disk located above said piston head, said flexible disk having a diameter larger than the diameter of said first bore of said cylindrical chamber so that when said plunger is inserted in said chamber of said barrel, said disk will flex concave rearwardly as said plunger moves forwardly in said barrel;
   e) said plunger and said disk moving from said first to said second bore when said syringe is used;
   f) said disk tending to reverse its flex to be forwardly concave as said plunger moves from said second to said first bore and said disk bears on said curved wall segment.

2. A single use hypodermic syringe according to claim 1, wherein said plunger includes a forward portion below said disk, said forward portion comprising a widened jamming section having a widest annular dimension being smaller than the diameter of said first bore of said cylinder, said disk having a thickness greater than the distance between the widest annular dimension of said jamming section and said diameter of the first bore so that sald jamming section jams the disk between the inner wall of the cylinder and the jamming section as the disk is moved rearwardly through the curved wall segment.

3. A single use hypodermic syringe as claimed in claim 1, wherein said plunger further includes a narrowed cylindrical portion adjacent said disk so that if said plunger is forcibly removed from said barrel, said disk and said piston head will separate at said narrowed portion, thereby preventing said syringe from being used again.

4. A single use hypodermic syringe as claimed in claim 2, wherein said plunger further includes a narrowed cylindrical portion adjacent said disk so that if said plunger is forcibly removed from said barrel, said disk and said piston head will separate at said narrowed portion, thereby preventing said syringe from being used again.

5. A single use hypodermic syringe as claimed in claim 1, further comprising a protective cap having an elongated rod extending from a wide end of said cap so that said cap can fit onto said forward end of said barrel before attachment of the hypodermic needle, with said elongated rod extending into said chamber past said curved wall segment to prevent said piston head from accidentally sliding past said first bore.

6. A single use hypodermic syringe as claimed in claim 2 further comprising a protective cap having an elongated rod extending from a wide end of said cap so that said cap can fit onto said forward end of said barrel before attachment of the hypodermic needle, with said elongated rod extending into said chamber past said curved wall segment to prevent said piston head from accidentally sliding past said first bore.

7. A single use hypodermic syringe as claimed in claim 1, further comprising means for restricting said plunger from being accidentally depressed all the way into said chamber of said barrel.

8. A single use hypodermic syringe as claimed in claim 2, further comprising means for restricting said plunger from being accidentally depressed all the way into said chamber of said barrel.

9. A single use hypodermic syringe as claimed in claim 7, wherein said restricting means is a limiting device insertable into said chamber of said rearward end of said barrel so that if said plunger is accidentally depressed said thumb rest will contact said limiting device and stop.

10. A single use hypodermic syringe as claimed in claim 8, wherein said restricting means is a limiting device insertable into said chamber of said rearward end of said barrel so that if said plunger is accidentally depressed said thumb rest will contact said limiting device and stop.

11. A single use hypodermic syringe as claimed in claim 7 wherein said restricting means is a limiting device connected to and extending upwardly from one side of said finger flange so that if said plunger is accidentally depressed, said thumb rest will contact said limiting device and stop.

12. A single use hypodermic syringe as claimed in claim 8 wherein said restricting means is a limiting device connected to and extending upwardly from one side of said finger flange so that if said plunger is accidentally depressed, said thumb rest will contact said limiting device and stop.

13. A single use hypodermic syringe as claimed in claim 11, wherein said limiting device includes a narrow tapered portion connected to said finger flange so that said limiting device can be easily broken off and removed therefrom to allow said plunger to be depressed into said barrel.

14. A single use hypodermic syringe as claimed in claim 12, wherein said limiting device includes a narrow tapered portion connected to said finger flange so that said limiting device can be easily broken off and removed therefrom to allow said plunger to be depressed into said barrel.

15. A single use hypodermic syringe as claimed in claim 1, further comprising a blocking member located between said plunger and said cylinder to prevent said plunger from being removed from said barrel prior to use of said syringe.

16. A single use hypodermic syringe as claimed in claim 2, further comprising a blocking member located between said plunger and said cylinder to prevent said plunger from being removed from said barrel prior to use of said syringe.

17. A single use hypodermic syringe as claimed in claim 15, wherein said blocking member comprises a cylindrical member movable with said plunger, said barrel comprising a reduced blocking wall located in the rear portion thereof preventing said cylindrical member and said plunger from being removed from said barrel.

18. A single use hypodermic syringe as claimed in claim 16, wherein said blocking member comprises a cylindrical member movable with said plunger, said barrel comprising a reduced blocking wall located in the rear portion thereof preventing said cylindrical member and said plunger from being removed from said barrel.

19. A single use hypodermic syringe as claimed in claim 1, wherein said curved wall segment comprises a rough surface.

20. A single use hypodermic syringe as claimed in claim 2, wherein said curved wall segment comprises a rough surface.

21. A single use hypodermic syringe as claimed in claim 1, further comprising locking means to lock said plunger into position with respect to said barrel when said plunger is fully depressed.

22. A single use hypodermic syringe as claimed in claim 21, wherein said locking means comprises a finger member attached to said barrel and a locking groove attached to said plunger whereby when said plunger is fully depressed, said finger member is captured in said locking groove.

23. A single use hypodermic syringe as claimed in claim 1, wherein the diameter of said disk is larger than the diameters of either said first or second bores.

24. A single use hypodermic syringe as claimed in claim 2, wherein the diameter of said disk is larger than the diameters of either said first or second bores.

* * * * *